United States Patent
Kameswaran

[11] Patent Number: 5,849,910
[45] Date of Patent: Dec. 15, 1998

[54] PROCESS FOR THE PREPARATION OF UNSYMMETRICAL 4,6-BIS ARYLOXY-PYRIMIDINE COMPOUNDS

[75] Inventor: Venkataraman Kameswaran, Princeton Junction, N.J.

[73] Assignee: American Cyanamid Company, Madison, N.J.

[21] Appl. No.: 929,293

[22] Filed: Sep. 5, 1997

[51] Int. Cl.⁶ .................. C07D 239/52; C07D 239/60
[52] U.S. Cl. ............... 544/319; 544/299; 544/301; 544/302; 544/303; 544/304
[58] Field of Search ............... 544/299, 301, 544/302, 303, 304, 319

[56] References Cited

U.S. PATENT DOCUMENTS 5,262,386  11/1993  Luthy et al. ............... 504/242

FOREIGN PATENT DOCUMENTS

| | | |
|---|---|---|
| 0382375 | 8/1990 | European Pat. Off. |
| 0468695 A1 | 1/1992 | European Pat. Off. |
| WO 92/08703 | 5/1992 | WIPO |
| WO 94/02470 | 2/1994 | WIPO |
| WO 95/05367 | 2/1995 | WIPO |
| WO 95/14674 | 6/1995 | WIPO |

OTHER PUBLICATIONS

K. Herman and G. Simche,m *Liebigs Ann. Chem.*. pp. 333–341 (1981).
K. Hafner and K.P. Meinhardt, *Org. Synth.*, 62, pp. 134–139 (1993).
H. Bredereck, et al., *Angew, Chem.* 72., p. 708, (1960).
G. L. Gafney and R. A. Jones, *Tetrahedron Letters*. pp. 2253–2256 (1982).

*Primary Examiner*—John M. Ford
*Attorney, Agent, or Firm*—Gregory M. Hill, Esq.

[57] ABSTRACT

This invention provides an improved process for the preparation of unsymmetrical 4,6-bis(aryloxy)pyrimidine compounds having the structural formula I

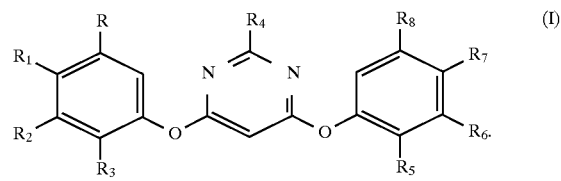

The unsymmetrical 4,6-bis(aryloxy)pyrimidine compounds are useful as pesticidal agents.

24 Claims, No Drawings

PROCESS FOR THE PREPARATION OF UNSYMMETRICAL 4,6-BIS ARYLOXY-PYRIMIDINE COMPOUNDS

BACKGROUND OF THE INVENTION

Symmetrical and unsymmetrical 4,6-bis(aryloxy) pyrimidine compounds which are useful as pesticidal agents are described in WO 94/02470. Symmetrical 4,6-bis(aryloxy)pyrimidine compounds are prepared in one step by reacting a 4,6-dihalopyrimidine compound with two molar equivalents of a phenol compound. In contrast, unsymmetrical 4,6-bis(aryloxy)pyrimidine compounds are significantly more difficult to prepare because the aryloxy groups must be introduced by separate reactions.

WO 94/02470 discloses that unsymmetrical 4,6-bis(aryloxy)pyrimidine compounds are prepared by reacting a 4,6-dihalopyrimidine compound with one molar equivalent of a first phenol compound in the presence of a base and then reacting the resulting compound with a second phenol compound in the presence of a base. However, that process is not entirely satisfactory for the commercial manufacture of unsymmetrical 4,6-bis(aryloxy)pyrimidine compounds. When 4,6-dichloropyrimidine is used, scrambling of the aryloxy groups occurs, producing symmetrical compounds which are difficult to separate from the desired unsymmetrical product, as shown in Flow Diagram I.

FLOW DIAGRAM I

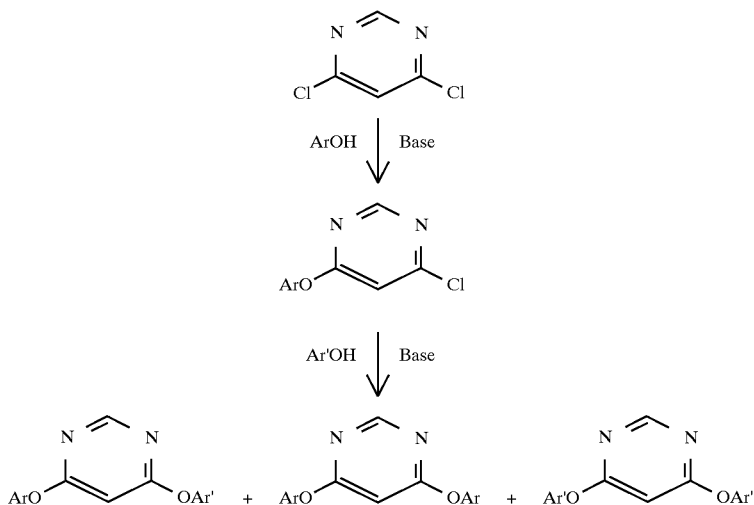

To overcome the scrambling problem associated with the use of 4,6-dichloropyrimidine, 4,6-difluoropyrimidine has been used. However, 4,6-difluoropyrimidine is prepared from 4,6-dichloropyrimidine by a halogen exchange reaction which requires the use of costly reagents and consumes a large amount of energy.

Co-pending U.S. patent application Ser. No. 08/813,947 filed on Mar. 3, 1997, discloses a process which overcomes the scrambling problem associated with the use of 4,6-dichloropyrimidine without requiring the use of 4,6-difluoropyrimidine. That application discloses that unsymmetrical 4,6-bis(aryloxy)pyrimidine compounds may be prepared by using an ammonium halide intermediate compound. However, the process disclosed in that application is not entirely satisfactory for the commercial manufacture of unsymmetrical 4,6-bis(aryloxy)pyrimidine compounds because the ammonium halide compound must be isolated and multiple solvent systems are used.

It is therefore an object of the present invention to provide an improved process for the preparation of unsymmetrical 4,6-bis(aryloxy)pyrimidine compounds which overcomes the problems associated with the processes of the art.

SUMMARY OF THE INVENTION

The present invention provides an improved process for the preparation of an unsymmetrical 4,6-bis(aryloxy) pyrimidine compound having the structural formula I

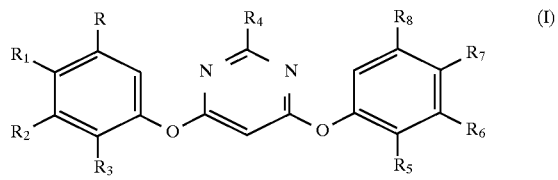

wherein

R and $R_8$ are each independently hydrogen or halogen;

$R_1$ and $R_7$ are each independently hydrogen, halogen, cyano, nitro, alkyl, haloalkyl, alkoxy, alkylthio, amino, alkylamino, dialkylamino, alkoxyalkyl, haloalkoxyalkyl or alkoxycarbonyl;

$R_2$ and $R_6$ are each independently hydrogen, halogen, alkyl, haloalkyl, haloalkoxy, haloalkylthio, haloalkenyl, haloalkynyl, haloalkoxyalkyl, alkoxycarbonyl, haloalkoxycarbonyl, haloalkylsulfinyl, haloalkylsulfonyl, nitro or cyano;

$R_3$ and $R_5$ are each independently hydrogen, halogen, alkyl or alkoxy; and $R_4$ is hydrogen, cyano, alkyl, haloalkyl, alkoxy, alkylthio, alkylsulfinyl or phenyl;

provided that at least one of $R_2$ and $R_6$ is other than hydrogen, and that the aryloxy groups are not the same; which process comprises reacting a 4-halo-6-(aryloxy) pyrimidine compound having the structural formula II

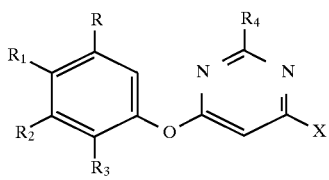

(II)

wherein R, $R_1$, $R_2$, $R_3$ and $R_4$ are as described above and X is Cl, Br or I with at least about one molar equivalent of a $C_1$–$C_4$trialkylamine, a 5- to 6-membered saturated or 5- to 14-membered unsaturated heterocyclic amine optionally substituted with one to three $C_1$–$C_4$alkyl groups or $C_1$–$C_4$alkoxy groups in the presence of a solvent selected from the group consisting of an aromatic hydrocarbon and a halogenated aromatic hydrocarbon and mixtures thereof to form an ammonium halide compound having the structural formula III

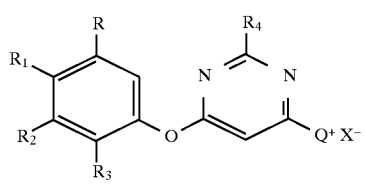

(III)

wherein R, $R_1$, $R_2$, $R_3$, $R_4$ and X are as described above, $Q^+$ is

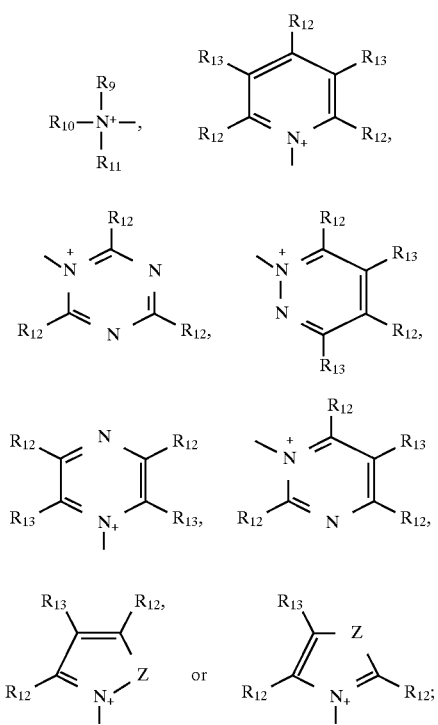

$R_9$, $R_{10}$ and $R_{11}$ are each independently $C_1$–$C_4$alkyl, and when taken together, $R_9$ and $R_{10}$ may form a 5- or 6-membered ring in which $R_9R_{10}$ is represented by the structure: —$(CH_2)_n$—, optionally interrupted by O, S or $NR_{14}$, where n is an integer of 3, 4 or 5, provided $R_{11}$ is $C_1$–$C_4$alkyl;

Z is O, S or $NR_{14}$, $R_{12}$ and $R_{13}$ are each independently hydrogen, $C_1$–$C_4$alkyl or $C_1$–$C_4$alkoxy, and when taken together, $R_{12}$ and $R_{13}$ may form a 5- or 6-membered saturated or unsaturated ring optionally interrupted by O, S or $NR_{14}$ and optionally substituted with one to three $C_1$–$C_4$alkyl groups or $C_1$–$C_4$alkoxy groups; and $R_{14}$ is $C_1$–$C_4$alkyl; and reacting the ammonium halide compound in situ with at least about one molar equivalent of a phenol compound having the structural formula IV

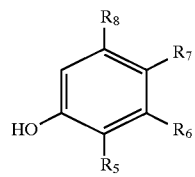

(IV)

wherein $R_5$, $R_6$, $R_7$ and $R_8$ are as described above and a base.

Advantageously, the process of this invention provides unsymmetrical 4,6-bis(aryloxy)pyrimidine compounds in higher yield than the art processes, overcomes the scrambling problem associated with the use of 4,6-dichloropyrimidine, uses less costly reagents than the 4,6-difluoropyrimidine art process, and avoids the isolation and multiple solvent requirements of the ammonium halide art process.

DETAILED DESCRIPTION OF THE INVENTION

The process of the present invention preferably comprises reacting a formula II 4-halo-6-(aryloxy)pyrimidine compound as described above with at least about one molar equivalent of the amine as described above in the presence of a solvent selected from the group consisting of an aromatic hydrocarbon and a halogenated aromatic hydrocarbon and mixtures thereof preferably at a temperature of about 0° C. to 100° C. to form a formula III ammonium halide compound as described above, and reacting the formula III compound in situ with at least about one molar equivalent of a formula IV phenol compound as described above and at least about one molar equivalent of the base preferably at a temperature of about 0° C. to 100° C. to form the desired unsymmetrical 4,6-bis(aryloxy)pyrimidine compound of formula I. The reaction scheme is shown in Flow Diagram II.

FLOW DIAGRAM II

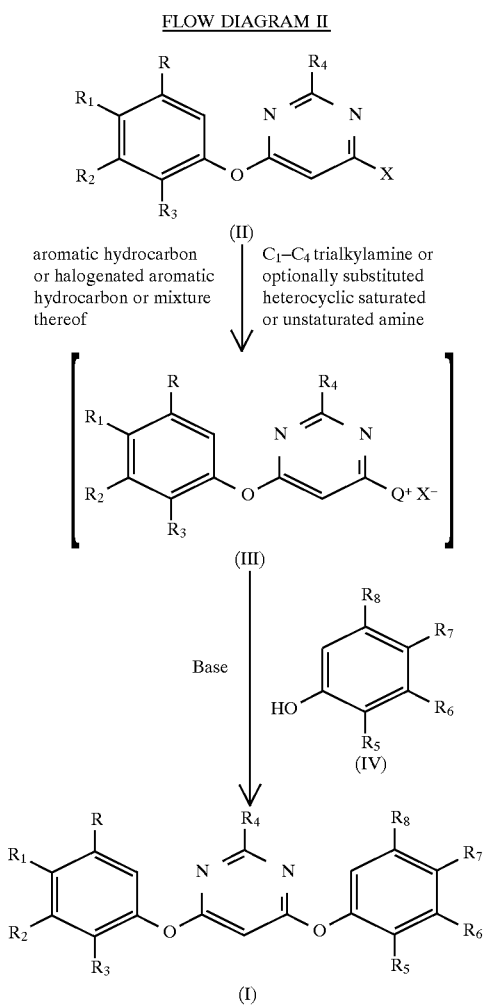

The formula I unsymmetrical 4,6-bis(aryloxy)pyrimidine compounds may be isolated by standard procedures known in the art.

Surprisingly, it has been found that unsymmetrical 4,6-bis(aryloxy)pyrimidine compounds are obtained in higher yield than the art processes when a formula III ammonium halide compound is reacted in situ with a formula IV phenol compound and a base in the presence of a solvent selected from the group consisting of an aromatic hydrocarbon, a halogenated aromatic hydrocarbon and mixtures thereof. Advantageously, the process of the present invention avoids the isolation requirement of the ammonium halide art process. In addition, the process of this invention uses significantly less solvent than the ammonium halide art process because the third solvent requirement of the art process is avoided by reacting the ammonium halide compound in situ with the phenol compound and base.

Aromatic hydrocarbons suitable for use in the process of the present invention include, but are not limited to, toluene, xylenes, benzene and the like and mixtures thereof with toluene being preferred. Halogenated aromatic hydrocarbons suitable for use include, but are not limited to, chlorobenzene, fluorobenzene, bromobenzene and the like and mixtures thereof.

The amines that may be used in the process of the invention to prepare the ammonium halide compounds are alkyl amines, 5- to 6-membered saturated and 5- to 14-membered unsaturated heterocyclic amines optionally substituted with one to three $C_1$–$C_4$alkyl groups or $C_1$–$C_4$alkoxy groups. The preferred amines are $C_1$–$C_4$trialkylamines, 5- to 6-membered saturated heterocyclic amines, and 5- to 14-membered unsaturated heterocyclic amines wherein the heterocyclic ring system contains one to three nitrogen atoms and optionally include sulfur or oxygen in the ring system.

The more preferred amines include trimethylamine, triethylamine, the saturated heterocyclic amines including, but not limited to, pyridines, picolines, pyrazines, pyridazines, triazines, quinolines, isoquinolines, imidazoles, benzothiazoles and benzimidazoles, optionally substituted with one to three $C_1$–$C_4$alkyl groups or $C_1$–$C_4$alkoxy groups, and unsaturated heterocyclic amines such as pyrrolidines, piperidines, piperazines, morpholines, thiazolidines and thiamorpholines.

Bases suitable for use in the process of the present invention include, but are not limited to, alkali metal carbonates such as sodium carbonate and potassium carbonate, alkaline earth metal carbonates such as calcium carbonate and magnesium carbonate, alkali metal hydrides such as sodium hydride and potassium hydride, alkali metal hydroxides such as sodium hydroxide and potassium hydroxide, and alkaline earth metal hydroxides such as calcium hydroxide and magnesium hydroxide, with alkali metal carbonates being preferred.

In formula I above, an alkyl group is suitably a straight chain or branched chain group containing up to 8 carbon atoms, for example up to 6 carbon atoms. Preferably, an alkyl group contains up to 4 carbon atoms. An alkyl moiety which forms part of another group, for example the alkyl of a haloalkyl group or each alkyl of an alkoxyalkyl group, suitably has up to 6 carbon atoms, preferably up to 4 carbon atoms.

In formula I above, halogen is fluorine, chlorine, bromine or iodine. Haloalkyl and haloalkoxy are especially trifluoromethyl, pentafluoroethyl and trifluoromethoxy.

The formula II compounds of the present invention may be prepared by reacting a 4,6-dihalopyrimidine compound of formula V

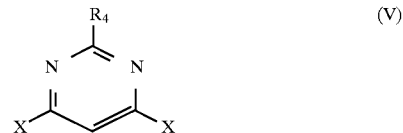

wherein $R_4$ is as described hereinabove and X is Cl, Br or I with up to one molar equivalent of a phenol compound of formula VI

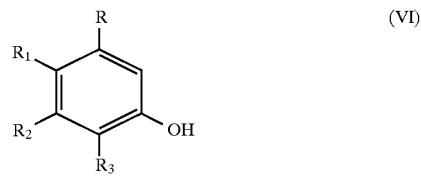

wherein R, $R_1$, $R_2$ and $R_3$ are as described hereinabove and a base in the presence of a solvent preferably at a temperature of about 0° C. to 100° C.

Bases suitable for use in the preparation of formula II compounds include, but are not limited to, alkali metal carbonates such as sodium carbonate and potassium carbonate, alkaline earth metal carbonates such as calcium carbonate and magnesium carbonate, alkali metal hydrides such as sodium hydride and potassium hydride, alkali metal hydroxides such as sodium hydroxide and potassium hydroxide, and alkaline earth metal hydroxides such as calcium hydroxide and magnesium hydroxide.

Solvents suitable for use in the preparation of formula II compounds include, but are not limited to, ethers such as diethyl ether, tetrahydrofuran and dioxane, carboxylic acid amides such as N,N-dimethylformamide and N,N-dimethylacetamide, halogenated hydrocarbons such as 1,2-dichloroethane, carbon tetrachloride, methylene chloride and chloroform, sulfoxides such as dimethyl sulfoxide, ketones such as acetone an N-methylpyrrolidone, aromatic hydrocarbons such as toluene, xylenes and benzene, halogenated aromatic hydrocarbons such as chlorobenzene, fluorobenzene and bromobenzene, and mixtures thereof, and mixtures with water. Preferred solvents for use in the preparation of formula II compounds include carboxylic acid amides, aromatic hydrocarbons, halogenated aromatic hydrocarbons, aromatic hydrocarbon/water mixtures, and halogenated aromatic hydrocarbon/water mixtures. It should be understood that when the solvent includes water, a base which is suitably stable in water should be used.

Advantageously, the overall process used to prepare the desired formula I compound from a 4,6-dihalopyrimidine compound of formula V may be integrated when the solvent used to prepare the formula II compound is an aromatic hydrocarbon/water or a halogenated aromatic hydrocarbon/water mixture. The integration is achieved by removing the water from the solvent system after the formula II compound is formed. The water may be removed using standard procedures such as decanting. The resultant aromatic hydrocarbon or halogenated aromatic hydrocarbon solvent, which contains the formula II compound, may then be used directly in the next step of the process.

The process of the present invention is especially useful for the preparation of formula I unsymmetrical 4,6-bis (aryloxy)pyrimidine compounds wherein R and $R_8$ are the same and each represents hydrogen or fluorine;

$R_1$ and $R_7$ are each independently hydrogen, halogen, cyano, nitro or $C_1$–$C_4$alkyl;

$R_2$ and $R_6$ are each independently hydrogen, fluorine, chlorine, $C_1$–$C_4$alkyl, $C_1$–$C_4$haloalkyl, $C_1$–$C_4$haloalkoxy, $C_2$–$C_4$haloalkenyl, $C_1$–$C_4$alkoxycarbonyl or nitro;

$R_3$ and $R_5$ are each independently hydrogen, halogen or $C_1$–$C_4$alkyl; and $R_4$ is hydrogen, $C_1$–$C_4$haloalkyl, $C_1$–$C_4$alkylthio or $C_1$–$C_4$alkylsulfinyl;

provided that at least one of $R_2$ and $R_6$ is other than hydrogen, and that the aryloxy groups are not the same.

In particular, the process of this invention is used to prepare unsymmetrical 4,6-bis(aryloxy)pyrimidine compounds of formula I wherein R, $R_3$, $R_4$, $R_5$ and $R_8$ are hydrogen; one of $R_1$ and $R_7$ is hydrogen, chlorine or cyano and the other is fluorine; and $R_2$ and $R_6$ are trifluoromethyl.

In order to facilitate a further understanding of the invention, the following examples are presented to illustrate more specific details thereof. The invention is not to be limited thereby except as defined in the claims.

EXAMPLE 1

Preparation of 4-[(4-Chloro-α,α,α-trifluoro-m-tolyl) oxy]-6-[(α,α, α,4-tetrafluoro-m-tolyl)oxy]pyrimidine from 4-chloro-6-[(α,α,α,4-tetrafluoro-m-tolyl)oxy]pyrimidine Invention Process

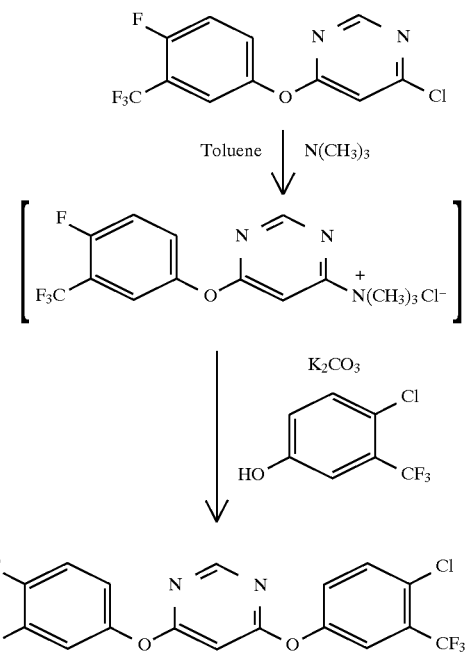

Trimethylamine (35.5 g, 0.6 mol) is bubbled through a mixture of 4-chloro-6-[(α,α,α,4-tetrafluoro-m-tolyl)oxy] pyrimidine (58.5 g, 0.2 mol) in toluene (250 mL) at room temperature over 2.5 hours. The resultant reaction mixture is stirred for 18 hours, treated with potassium carbonate (27.6 g, 0.2 mol) and α,α,α-trifluoro-4-chloro-m-cresol (39.3 g, 0.2 mol), stirred for three hours, and diluted with water. The phases are separated and the organic phase is washed sequentially with 5% sodium hydroxide solution and water, and concentrated in vacuo to obtain an oil. The oil is crystallized from heptane to give the title product as a solid (86.2 g, 96.2% pure, 91.6% isolated yield).

As can be seen from the data in Example 1, the title product is prepared in 91.6% yield starting from 4-chloro-6-[(α,α,α,4-tetrafluoro-m-tolyl)oxy]pyrimidine.

EXAMPLE 2

Preparation of 4-[(4-Chloro-α,α,α-trifluoro-m-tolyl) oxy]-6-[(α,α,α,4-tetrafluoro-m-tolyl)oxy]pyrimidine from 4-chloro-6-[(α,α,α,4-tetrafluoro-m-tolyl)oxy]pyrimidine Art Process a) Preparation of Trimethyl{6-[(α,α,α,4-tetrafluoro-m-tolyl)oxy]-4-pyrimidyl}ammonium chloride

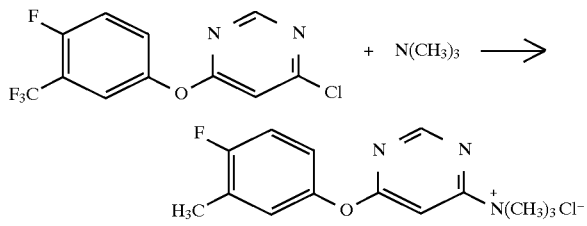

Liquefied trimethylamine (1,255 g, 21.24 mol) is added to a solution of 4-chloro-6-[(α,α,α,4-tetrafluoro-m-tolyl)oxy] pyrimidine (2,038.8 g, 6.97 mol) in toluene (17 L). The reaction mixture is stirred overnight at room temperature and filtered. The resultant solid is washed sequentially with toluene and hexanes and dried overnight in a vacuum oven at 60°–65° C. to obtain the title product as a white solid (1,962 g, 80% yield).

b) Preparation of 4-[(4-Chloro-α,α,α,-trifluoro-m-tolyl)oxy]-6-[(α,α,α,4-tetrafluoro-m-tolyl)oxy]pyrimidine

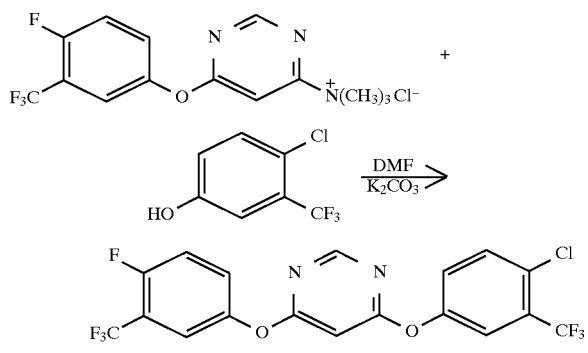

α,α,α-Trifluoro-4-chloro-m-cresol (1,118.9 g, 5.69 mol) is added to a mixture of trimethyl{6-[(α,α,α,4-tetrafluoro-m-tolyl)oxy]-4-pyrimidyl}ammonium chloride (1,962.0 g, 5.58 mol) and potassium carbonate (793.2 g, 5.74 mol) in N,N-dimethylformamide (8.5 L). The reaction mixture is stirred overnight at room temperature, cooled to 5° C. and slowly diluted with water (2.27 L). The resultant aqueous mixture is filtered to give a solid. The solid is washed sequentially with water, hexanes and water, dried overnight in a vacuum oven at 40°–45° C. and recrystallized from hexanes to obtain the title product as a yellow solid (1,731.5 g, 69% yield).

As can be seen from the data in Example 2, the art process provides the title product in 55.2% yield starting from 4-chloro-6-[(α,α,α,4-tetrafluoro-m-tolyl)oxy]pyrimidine.

Advantageously, the process of the present invention provides 4-[(4-chloro-α,α,α-trifluoro-m-tolyl)oxy]-6-[(α,α,α,4-tetrafluoro-m-tolyl)oxy]pyrimidine in significantly higher yield starting from 4-chloro-6-[(α,α,α,4-tetrafluoro-m-tolyl)oxy]pyrimidine than the art process (91.6% vs. 55.2%).

EXAMPLE 3

Preparation of 4-[(4-Chloro-α,α,α-trifluoro-m-tolyl)oxy]-6-[(α,α,α,4-tetrafluoro-m-tolyl)oxy]pyrimidine from 2,6-dichloropyrimidine and α,α,α,4-tetrafluoro-m-cresol Invention Process a) Preparation of 4-Chloro-6-[(α,α,α,4-tetrafluoro-m-tolyl)oxy]pyrimidine

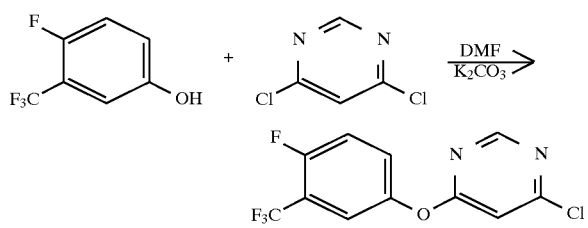

A mixture of 4,6-dichloropyrimidine (119.2 g, 0.8 mol) and potassium carbonate (110.6 g, 0.8 mol) in N,N-dimethylformamide (585 mL) is treated with α,α,α,4-tetrafluoro-m-cresol (144.1 g, 0.8 mol) over 20 minutes, stirred at 45° C. for 5 hours, stirred overnight at room temperature, and diluted with water (1200 mL). The resultant aqueous mixture is extracted with methylene chloride. The organic extracts are combined, washed sequentially with 5% sodium hydroxide solution and water, and concen-trated in vacuo to obtain an oil (248.1 g, 79.4% yield based on an assay of the toluene solution used in step (b)).

b) Preparation of 4-[(4-Chloro-α,α,α-trifluoro-m-tolyl)oxy]-6-[(α,α,α,4-tetrafluoro-m-tolyl)oxy]pyrimidine

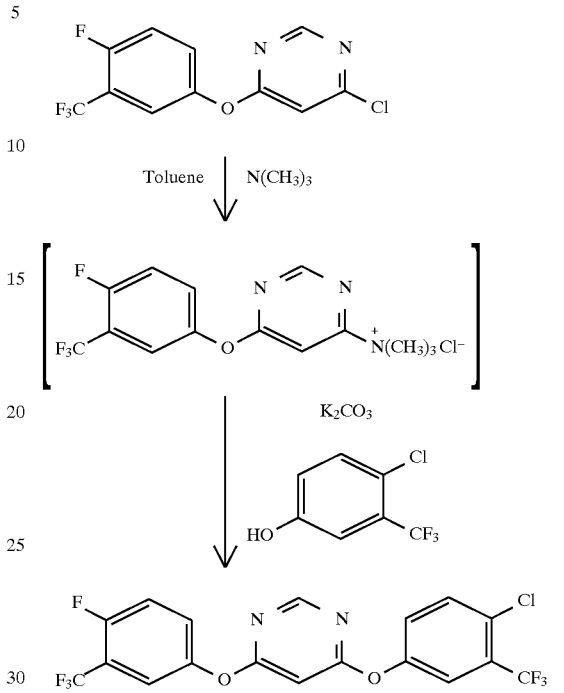

Trimethylamine gas (127.6 g, 2.16 mol) is bubbled through a solution of all of the 4-chloro-6-[(α,α,α,4-tetrafluoro-m-tolyl)oxy]pyrimidine obtained in step (a) in toluene (800 mL) over 2.5 hours. The resulting mixture is stirred for 18 hours, treated with potassium carbonate (99.8 g, 0.72 mol) and α,α,α-trifluoro-4-chloro-m-cresol (141.7 g, 0.72 mol) over 20 minutes, stirred at room temperature for 5 hours, diluted with water (800 mL), and stirred for 15 minutes. The phases are separated and the organic phase is washed with water, and concentrated in vacuo to obtain an oil. The oil is crystallized from heptane to give the title product as a yellow solid (271.1 g, 89.7% pure, 67.2% isolated yield, 6.8% left in the mother liquor).

As can be seen from the data in Example 3, the title product is prepared in 67% isolated yield starting from 4,6-dichloropyrimidine and α,α,α,4-tetrafluoro-m-cresol.

EXAMPLE 4

Preparation of 4-[(4-Chloro-α,α,α-trifluoro-m-tolyl)oxy]-6-[(α,α,α,4-tetrafluoro-m-tolyl)oxy]pyrimidine from 2,6-dichloropyrimidine and α,α,α,4-tetrafluoro-m-cresol Art Process a) Preparation of 4-Chloro-6-[(α,α,α,4-tetrafluoro-m-tolyl)oxy]pyrimidine

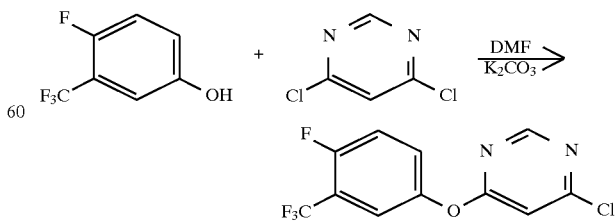

α,α,α,4-Tetrafluoro-m-cresol (1,208.9 g, 6.71 mol) is slowly added to a mixture of 4,6-dichloropyrimidine (1,000.0 g, 6.71 mol) and potassium carbonate (967.5 g, 7.00 mol) in N,N-dimethylformamide (10 L). The reaction mixture is stirred overnight at room temperature, stirred at 45° C. for 2 hours, stirred at 71° C. for 2 hours, stirred overnight at room temperature and poured into water (20 L). The resultant aqueous mixture is extracted with methylene chloride. The organic extracts are combined, washed sequentially with water, 5% sodium hydroxide solution and brine, dried over anhydrous magnesium sulfate and concentrated in vacuo to obtain the title product as a brown oil (1,943.3 g, 99% yield).

b) Preparation of Trimethyl{6-[(α,α,α,4-tetrafluoro-m-tolyl)oxy]-4-pyrimidyl}ammonium chloride

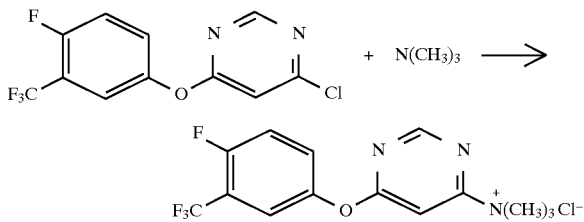

Liquefied trimethylamine (1,255 g, 21.24 mol) is added to a solution of 4-chloro-6-[(α,α,α,4-tetrafluoro-m-tolyl)oxy]pyrimidine (2,038.8 g, 6.97 mol) (17 L). The reaction mixture is stirred overnight at room temperature and filtered. The resultant solid is washed sequentially with toluene and hexanes and dried overnight in a vacuum oven at 60°–65° C. to obtain the title product as a white solid (1,962 g, 80% yield).

c) Preparation of 4-[(4-Chloro-α,α,α-trifluoro-m-tolyl)oxy]-6-[(α,α,α,4-tetrafluoro-m-tolyl)oxy]pyrimidine

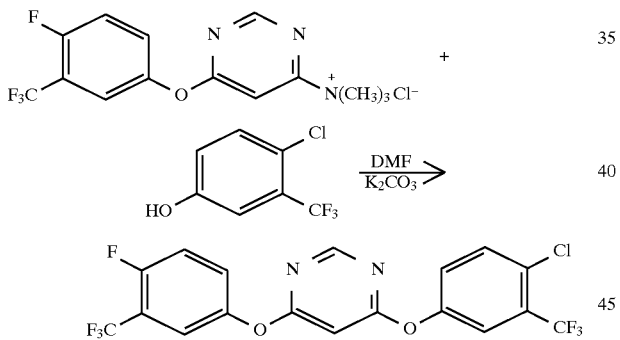

α,α,α-Trifluoro-4-chloro-m-cresol (1,118.9 g, 5.69 mol) is added to a mixture of trimethyl{6-[(α,α,α,4-tetrafluoro-m-tolyl)oxy]-4-pyrimidyl}ammonium chloride (1,962.0 g, 5.58 mol) and potassium carbonate (793.2 g, 5.74 mol) in N,N-dimethylformamide (8.5 L). The reaction mixture is stirred overnight at room temperature, cooled to 5° C. and slowly diluted with water (2.27 L). The resultant aqueous mixture is filtered to give a solid. The solid is washed sequentially with water, hexanes and water, dried overnight in a vacuum oven at 40°–45° C. and recrystallized from hexanes to obtain the title product as a yellow solid (1,731.5 g, 69% yield).

As can be seen from the data in Example 4, the art process provides the title product in 55% overall yield starting from 4,6-dichloropyrimidine and α,α,α,4-tetrafluoro-m-cresol.

Advantageously, the process of the present invention provides 4-[(4-chloro-α,α,α-trifluoro-m-tolyl)oxy]-6-[(α,α,α,4-tetrafluoro-m-tolyl)oxy]pyrimidine in significantly higher yield starting from 4,6-dichloropyrimidine and α,α,α,4-tetrafluoro-m-cresol than the art process (67% vs. 55%).

EXAMPLE 5

Preparation of 4-[(4-Chloro-α,α,α-trifluoro-m-tolyl)oxy]-6-[(α,α,α,4-tetrafluoro-m-tolyl)oxy]pyrimidine from 2,6-dichloropyrimidine and α,α,α-trifluoro-4-chloro-m-cresol Invention process a) Preparation of 4-Chloro-6-[(4-chloro-α,α,α-trifluoro-m-tolyl)oxy]pyrimidine

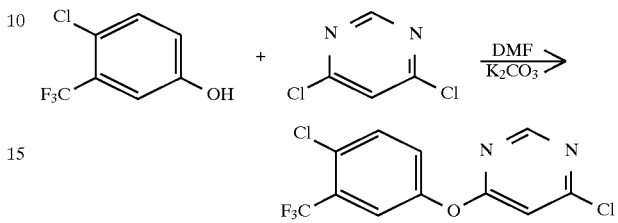

A mixture of 4,6-dichloropyrimidine (119.2 g, 0.8 mol) and potassium carbonate (110.6 g, 0.8 mol) in N,N-dimethylformamide (585 mL) is treated with α,α,α-trifluoro-4-chloro-m-cresol (157.3 g, 0.8 mol) over 20 minutes, stirred at 45° C. for 5 hours, stirred overnight at room temperature, and diluted with water (1200 mL). The resultant aqueous mixture is extracted with methylene chloride. The organic extracts are combined, washed sequentially with 5% sodium hydroxide solution and water, and concentrated in vacuo to obtain the title product as an oil (249.4 g).

b) Preparation of 4-[(4-Chloro-α,α,α-trifluoro-m-tolyl)oxy]-6-[(α,α,α,4-tetrafluoro-m-tolyl)oxy]pyrimidine

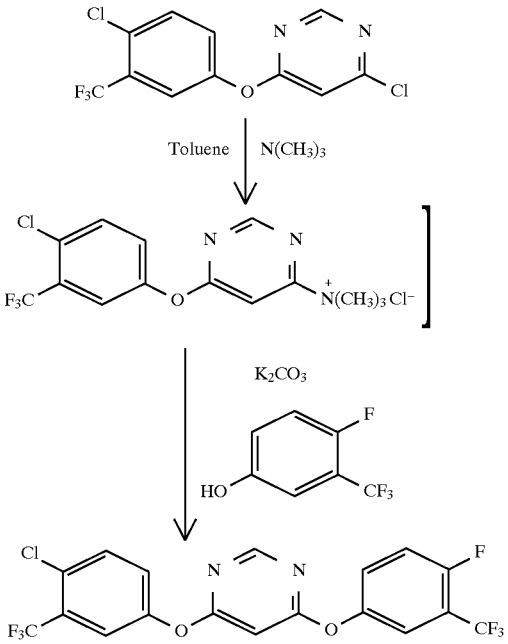

Trimethylamine gas (127.6 g, 2.16 mol) is bubbled through a solution of all of the 4-chloro-6-[(4-chloro-α,α,α-trifluoro-m-tolyl)oxy]pyrimidine obtained in step (a) in toluene (800 mL) over 2.5 hours. The resulting mixture is stirred for 18 hours, treated with potassium carbonate (99.5 g, 0.72 mol) and α,α,α,4-tetrafluoro-m-cresol (129.7 g, 0.72 mol) over 20 minutes, stirred at room temperature for 5 hours, diluted with water (800 mL), and stirred for 15 minutes. The phases are separated and the organic phase is washed with water, and concentrated in vacuo to obtain an oil. The oil is crystallized from heptane to give the title product as a yellow solid (273.4 g, 92.8% pure, 70% isolated yield).

As can be seen from the data in Example 5, the title product is prepared in 70% yield starting from 4,6-dichloropyrimidine and α,α,α-trifluoro-4-chloro-m-cresol.

EXAMPLE 6

Preparation of 4-Chloro-6-[(α,α,α,4-tetrafluoro-m-tolyl)oxy]pyrimidine using a toluene/water mixture as the solvent

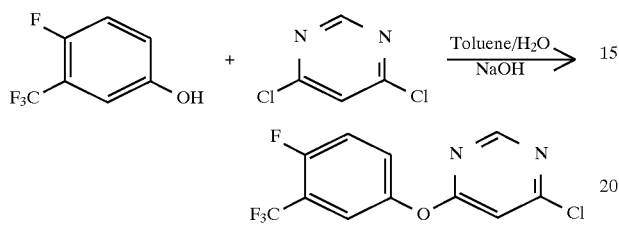

A mixture of 4,6-dichloropyrimidine (14.9 g, 0.1 mol) and α,α,α,4-tetrafluoro-m-cresol (18.0 g, 0.1 mol) in toluene (100 mL) and water (25 mL) is treated with 50% sodium hydroxide solution (8.0 g, 0.1 mol), stirred at 78° C. for 6 hours, cooled, and diluted with water. The phases are separated and the organic phase is concentrated in vacuo to obtain the title product as an oil (27.0 g, 70% real yield by HPLC). When the reaction is repeated using benzyltriethylammonium chloride (10 mol %) as a catalyst, the reaction yield is 72.3%.

I claim:

1. In a process for the preparation of an unsymmetrical 4,6-bis(aryloxy)pyrimidine compound having the structural formula I

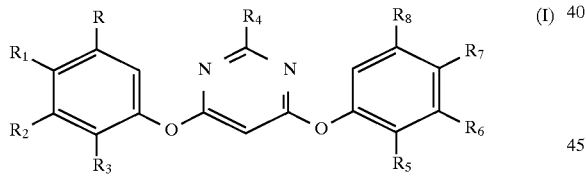

wherein

R and $R_8$ are each independently hydrogen or halogen;

$R_1$ and $R_7$ are each independently hydrogen, halogen, cyano, nitro, alkyl, haloalkyl, alkoxy, alkylthio, amino, alkylamino, dialkylamino, alkoxyalkyl, haloalkoxyalkyl or alkoxycarbonyl;

$R_2$ and $R_6$ are each independently hydrogen, halogen, alkyl, haloalkyl, haloalkoxy, haloalkylthio, haloalkenyl, haloalkynyl, haloalkoxyalkyl, alkoxycarbonyl, haloalkoxycarbonyl, haloalkylsulfinyl, haloalkylsulfonyl, nitro or cyano;

$R_3$ and $R_5$ are each independently hydrogen, halogen, alkyl or alkoxy; and $R_4$ is hydrogen, cyano, alkyl, haloalkyl, alkoxy, alkylthio, alkylsulfinyl or phenyl;

provided that at least one of $R_2$ and $R_6$ is other than hydrogen, and that the aryloxy groups are not the same; the improvement comprises reacting a 4-halo-6-(aryloxy)pyrimidine compound having the structural formula II

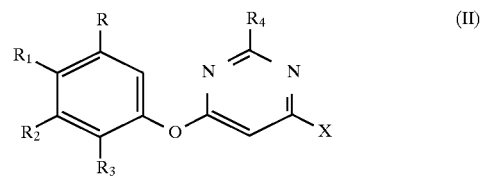

wherein R, $R_1$, $R_2$, $R_3$ and $R_4$ are as described above and X is Cl, Br or I with at least about one molar equivalent of a $C_1$–$C_4$trialkylamine, a 5- to 6-membered saturated or 5- to 14-membered unsaturated heterocyclic amine optionally substituted with one to three $C_1$–$C_4$alkyl groups or $C_1$–$C_4$alkoxy groups in the presence of a solvent selected from the group consisting of an aromatic hydrocarbon and a halogenated aromatic hydrocarbon and mixtures thereof to form an ammonium halide compound having the structural formula III

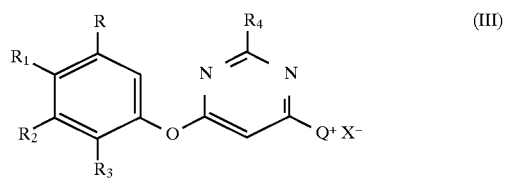

wherein R, $R_1$, $R_2$, $R_3$, $R_4$ and X are as described above, $Q^+$ is

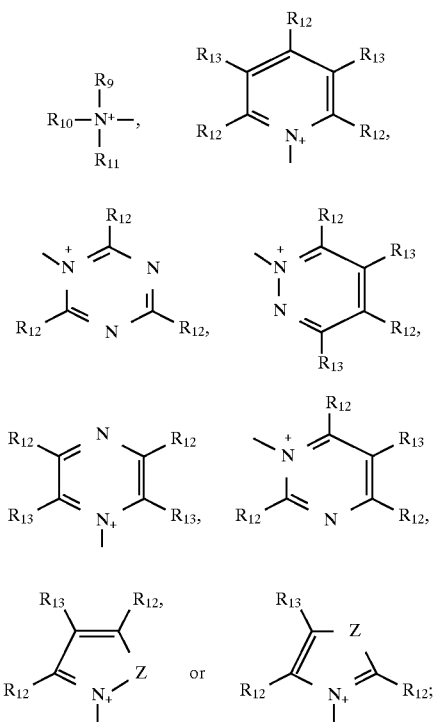

$R_9$, $R_{10}$ and $R_{11}$ are each independently $C_1$–$C_4$alkyl, and when taken together, $R_9$ and $R_{10}$ may form a 5- or 6-membered ring in which $R_9R_{10}$ is represented by the structure: —$(CH_2)_n$—, optionally interrupted by O, S or $NR_{14}$, where n is an integer of 3, 4 or 5, provided $R_{11}$ is $C_1$–$C_4$alkyl;

Z is O, S or $NR_{14}$, $R_{12}$ and $R_{13}$ are each independently hydrogen, $C_1$–$C_4$alkyl or $C_1$–$C_4$alkoxy, and when taken together, $R_{12}$ and $R_{13}$ may form a 5- or 6-membered saturated or unsaturated ring optionally interrupted by O, S or $NR_{14}$ and optionally substituted with one to three $C_1-C_4$alkyl groups or $C_1-C_4$alkoxy groups; and $R_{14}$ is $C_1-C_4$alkyl; and reacting the ammonium halide compound in situ with at least about one molar equivalent of a phenol compound having the structural formula IV

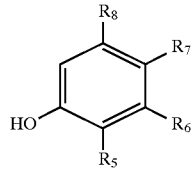
(IV)

wherein $R_5$, $R_6$, $R_7$ and $R_8$ are as described above and a base.

2. The process according to claim 1 wherein the solvent is selected from the group consisting of toluene, a xylene, benzene and chlorobenzene and mixtures thereof.

3. The process according to claim 2 wherein the solvent is toluene.

4. The process according to claim 1 wherein the base is selected from the group consisting of an alkali metal carbonate, an alkaline earth metal carbonate, an alkali metal hydride, an alkali metal hydroxide and an alkaline earth metal hydroxide.

5. The process according to claim 4 wherein the base is an alkali metal carbonate.

6. The process according to claim 1 wherein X is Cl.

7. The process according to claim 1 wherein $Q^+$ is

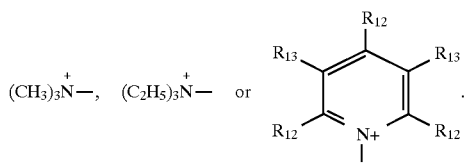

8. The process according to claim 7 wherein $Q^+$ is $(CH_3)_3$

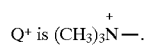

9. The process according to claim 1 wherein the 4-halo-6-(aryloxy)pyrimidine compound is reacted with the amine at a temperature of about 0° C. to 100° C., and the ammonium halide compound is reacted with the phenol compound and the base at a temperature of about 0° C. to 100° C.

10. The process according to claim 1 wherein

R and $R_8$ are the same and each represents hydrogen or fluorine;

$R_1$ and $R_7$ are each independently hydrogen, halogen, cyano, nitro or $C_1-C_4$alkyl;

$R_2$ and $R_6$ are each independently hydrogen, fluorine, chlorine, $C_1-C_4$alkyl, $C_1-C_4$haloalkyl, $C_1-C_4$haloalkoxy, $C_2-C_4$haloalkenyl, $C_1-C_4$alkoxycarbonyl or nitro;

$R_3$ and $R_5$ are each independently hydrogen, halogen or $C_1-C_4$alkyl; and $R_4$ is hydrogen, $C_1-C_4$haloalkyl, $C_1-C_4$alkylthio or $C_1-C_4$alkylsulfinyl.

11. The process according to claim 10 wherein

R, $R_3$, $R_4$, $R_5$ and $R_8$ are hydrogen;

one of $R_1$ and $R_7$ is hydrogen, chlorine or cyano and the other is fluorine; and $R_2$ and $R_6$ are trifluoromethyl.

12. In a process for the preparation of an unsymmetrical 4,6-bis(aryloxy)pyrimidine compound having the structural formula I

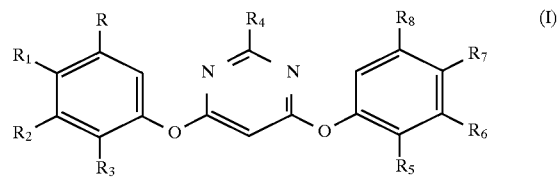
(I)

wherein

R and $R_8$ are each independently hydrogen or halogen;

$R_1$ and $R_7$ are each independently hydrogen, halogen, cyano, nitro, alkyl, haloalkyl, alkoxy, alkylthio, amino, alkylamino, dialkylamino, alkoxyalkyl, haloalkoxyalkyl or alkoxycarbonyl;

$R_2$ and $R_6$ are each independently hydrogen, halogen, alkyl, haloalkyl, haloalkoxy, haloalkylthio, haloalkenyl, haloalkynyl, haloalkoxyalkyl, alkoxycarbonyl, haloalkoxycarbonyl, haloalkylsulfinyl, haloalkylsulfonyl, nitro or cyano;

$R_3$ and $R_5$ are each independently hydrogen, halogen, alkyl or alkoxy; and $R_4$ is hydrogen, cyano, alkyl, haloalkyl, alkoxy, alkylthio, alkylsulfinyl or phenyl;

provided that at least one of $R_2$ and $R_6$ is other than hydrogen, and that the aryloxy groups are not the same; the improvement comprises reacting a 4,6-dihalopyrimidine compound having the structural formula V

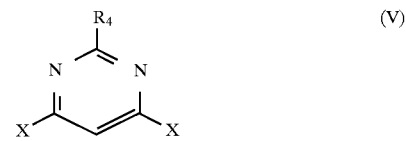
(V)

wherein $R_4$ is as described above and X is Cl, Br or I with up to one molar equivalent of a first phenol compound having the structural formula VI

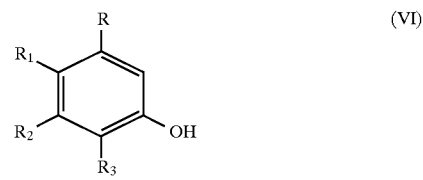
(VI)

wherein R, $R_1$, $R_2$ and $R_3$ are as described above and a first base in the presence of a first solvent to form a 4-halo-6-(aryloxy)pyrimidine compound having the structural formula II

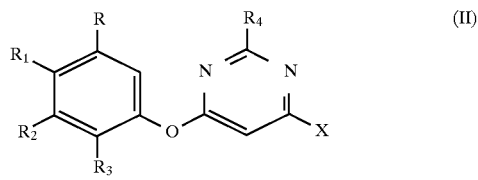
(II)

wherein R, $R_1$, $R_2$, $R_3$, $R_4$ and X are as described above, reacting the 4-halo-6-(aryloxy)pyrimidine compound with at least about one molar equivalent of a $C_1-C_4$trialkylamine, a 5- to 6-membered saturated or 5- to 14-membered unsaturated heterocyclic amine optionally substituted with one to three $C_1-C_4$alkyl groups or $C_1-C_4$alkoxy groups in the presence of a second solvent selected from the group consisting of an aromatic hydrocarbon and a halogenated aromatic hydrocarbon and mixtures thereof to form an ammonium halide compound having the structural formula III

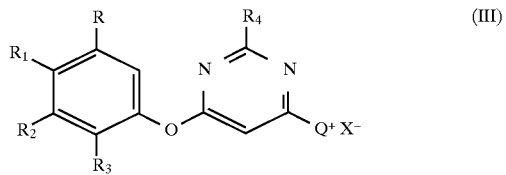 (III)

wherein R, $R_1$, $R_2$, $R_3$, $R_4$ and X are as described above, $Q^+$ is

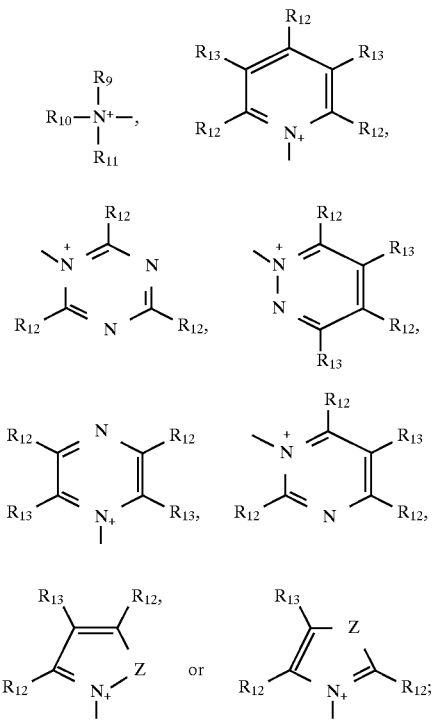

$R_9$, $R_{10}$ and $R_{11}$ are each independently $C_1$–$C_4$alkyl, and when taken together, $R_9$ and $R_{10}$ may form a 5- or 6-membered ring in which $R_9R_{10}$ is represented by the structure: —$(CH_2)_n$—, optionally interrupted by O, S or $NR_{14}$, where n is an integer of 3, 4 or 5, provided $R_{11}$ is $C_1$–$C_4$alkyl;

Z is O, S or $NR_{14}$, $R_{12}$ and $R_{13}$ are each independently hydrogen, $C_1$–$C_4$alkyl or $C_1$–$C_4$alkoxy, and when taken together, $R_{12}$ and $R_{13}$ may form a 5- or 6-membered saturated or unsaturated ring optionally interrupted by O, S or $NR_{14}$ and optionally substituted with one to three $C_1$–$C_4$alkyl groups or $C_1$–$C_4$alkoxy groups; and $R_{14}$ is $C_1$–$C_4$alkyl; and reacting the ammonium halide compound in situ with at least about one molar equivalent of a second phenol compound having the structural formula IV

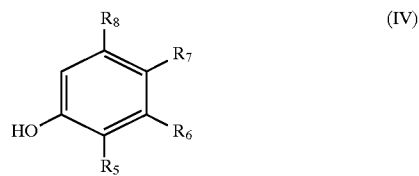 (IV)

wherein $R_5$, $R_6$, $R_7$ and $R_8$ are as described above and a second base.

13. The process according to claim 12 wherein the first solvent is selected from the group consisting of an ether, a carboxylic acid amide, a halogenated hydrocarbon, an aromatic hydrocarbon, a halogenated aromatic hydrocarbon, a sulfoxide and a ketone and mixtures thereof and mixtures with water.

14. The process according to claim 13 wherein the first solvent is selected from the group consisting of a carboxylic acid amide, an aromatic hydrocarbon/water mixture and a halogenated aromatic hydrocarbon/water mixture.

15. The process according to claim 12 wherein the second solvent is selected from the group consisting of toluene, a xylene, benzene and chlorobenzene and mixtures thereof.

16. The process according to claim 15 wherein the second solvent is toluene.

17. The process according to claim 12 wherein the first and second bases are selected from the group consisting of an alkali metal carbonate, an alkaline earth metal carbonate, an alkali metal hydride, an alkali metal hydroxide and an alkaline earth metal hydroxide.

18. The process according to claim 17 wherein the first base is selected from the group consisting of an alkali metal carbonate and an alkali metal hydroxide, and the second base is an alkali metal carbonate.

19. The process according to claim 12 wherein X is Cl.

20. The process according to claim 12 wherein $Q^+$ is

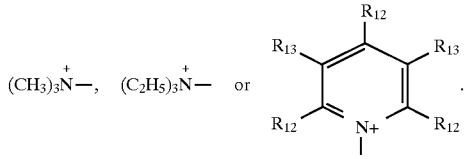

21. The process according to claim 20 wherein $Q^+$ is $(CH_3)_3$ $Q^+$ is $(CH_3)_3\overset{+}{N}-$.

22. The process according to claim 12 wherein the 4,6-dihalopyrimidine compound is reacted with the first phenol compound and the first base at a temperature of about 0° C. to 100° C., the 4-halo-6-(aryloxy)pyrimidine compound is reacted with the amine at a temperature of about 0° C. to 100° C., and the ammonium halide compound is reacted with the second phenol compound and the second base at a temperature of about 0° C. to 100° C.

23. The process according to claim 12 wherein
R and $R_8$ are the same and each represents hydrogen or fluorine;
$R_1$ and $R_7$ are each independently hydrogen, halogen, cyano, nitro or $C_1$–$C_4$alkyl;
$R_2$ and $R_6$ are each independently hydrogen, fluorine, chlorine, $C_1$–$C_4$alkyl, $C_1$–$C_4$haloalkyl, $C_1$–$C_4$haloalkoxy, $C_2$–$C_4$haloalkenyl, $C_1$–$C_4$alkoxycarbonyl or nitro;

$R_3$ and $R_5$ are each independently hydrogen, halogen or $C_1$–$C_4$alkyl; and $R_4$ is hydrogen, $C_1$–$C_4$haloalkyl, $C_1$–$C_4$alkylthio or $C_1$–$C_4$alkylsulfinyl.

24. The process according to claim 23 wherein

R, $R_3$, $R_4$, $R_5$ and $R_8$ are hydrogen;

one of $R_1$ and $R_7$ is hydrogen, chlorine or cyano and the other is fluorine; and $R_2$ and $R_6$ are trifluoromethyl.

* * * * *